United States Patent [19]

Sagane et al.

[11] Patent Number: 5,106,931

[45] Date of Patent: Apr. 21, 1992

[54] COPOLYMERIZATION OF ETHYLENE AND CYCLOOLEFIN ISOMERIZED FROM ENDO-FORM TO EXO-FORM

[75] Inventors: Toshihiro Sagane; Hideaki Yamaguchi, both of Iwakuni; Shuji Minami, Ohtake; Akira Mizuno, Ohno; Hiroo Wamura, Waki, all of Japan

[73] Assignee: Mitsui Petrochemical Industries Ltd., Tokyo, Japan

[21] Appl. No.: 565,143

[22] Filed: Aug. 10, 1990

[30] Foreign Application Priority Data

| Aug. 15, 1989 | [JP] | Japan | 1-210448 |
| Aug. 15, 1989 | [JP] | Japan | 1-210449 |
| Sep. 20, 1989 | [JP] | Japan | 1-244493 |
| Sep. 20, 1989 | [JP] | Japan | 1-244494 |
| Oct. 23, 1989 | [JP] | Japan | 1-275714 |
| Oct. 23, 1989 | [JP] | Japan | 1-275715 |

[51] Int. Cl.$^5$ ............ C08F 210/02; C08F 2/06
[52] U.S. Cl. ............ 526/282; 526/75; 526/169.2; 526/281
[58] Field of Search ............ 526/281, 282, 283, 169.2, 526/75

[56] References Cited

U.S. PATENT DOCUMENTS

| 4,614,778 | 9/1986 | Kajiura et al. | 526/281 |
| 4,689,380 | 8/1987 | Nahm | 526/283 |
| 4,804,795 | 2/1989 | Yuasa et al. | 585/21 |

FOREIGN PATENT DOCUMENTS 0294998 12/1988 European Pat. Off. ............ 526/281

Primary Examiner—Fred Teskin
Attorney, Agent, or Firm—Sherman and Shalloway

[57] ABSTRACT

This invention is to provide a novel process for the isomerization of a cycloolefin having an endo form to a cycloolefin having an exo form. The resulting isomer mixture has a novel composition, and a random copolymer produced from the above compositionally novel isomer mixture and ethylene has an excellent heat resistance and mechanical strength.

8 Claims, 2 Drawing Sheets

COPOLYMERIZATION OF ETHYLENE AND CYCLOOLEFIN ISOMERIZED FROM ENDO-FORM TO EXO-FORM

FIELD OF THE INVENTION

This invention relates to isomerization of a cycloolefin such as tetracyclododecene or pentacyclopentadecene from an endo form to an exo form and to copolymerization of a cycloolefin and ethylene.

The present applicants found that cycloolefin random copolymers obtained by copolymerization of ethylene and tetracyclododecenes are synthetic resins having excellent transparency and well-balanced properties among heat resistance, thermal aging resistance, chemical resistance, solvent resistance, dielectric properties, mechanical properties and that such cycloolefin random copolymers exhibit excellent performance in a field of optical materials such as optical memory disks and fibers. Therefore, the present applicants already proposed such random copolymers in Japanese Laid-Open Patent Publications Nos. 168708/1985, 98780/1986, 115912/1986, 115916/1986, 120816/1986, and 252407/1987.

Tetracyclododecenes used for production of such random copolymers are prepared by a Diels-Alder reaction between corresponding norbornenes and cyclopentadienes.

In this Diels-Alder reaction, cis addition dominantly proceeds. For example, in a reaction between cyclopentadiene (a) and norbornene (b), tetracyclododecene having an endo form (c) is mainly formed as shown in the following reaction formula.

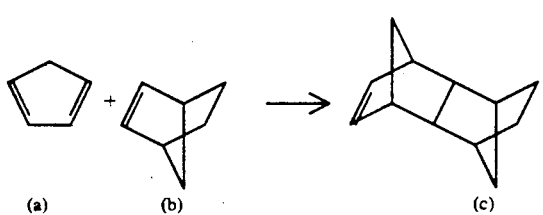

(a)   (b)   (c)

The following formula is rarely formed.

(d)

It is also known that cycloolefin random copolymers produced by copolymerizing tetracyclododecenes mainly having an endo form prepared by the above Diels-Alder reaction with ethylene exhibit excellent heat resistance and mechanical strength.

International Laid-Open Publication No. WO89/01950 describes that cycloolefin random copolymers obtained by copolymerization of ethylene with pentacyclopentadecenes (cycloolefins) have excellent transparency and are excellent not only in optical properties such as optical uniformity and small birefringence but also in other properties such as heat resistance, chemical resistance, dimensional stability and mechanical properties.

Pentacyclopentadecenes used as a cycloolefin for production of such random copolymers are also prepared by a Diels-Alder reaction between corresponding dihydrodicyclopentadienes (partially hydrogenated products of dicyclopentadienes) and cyclopentadienes.

For example, in a reaction between cyclopentadiene (a) and dihydrodicyclopentadiene (e), pentacyclopentadecene having an endo form (f) is mainly formed as shown in the following reaction formula in the same manner as the preparation of tetracyclododecene.

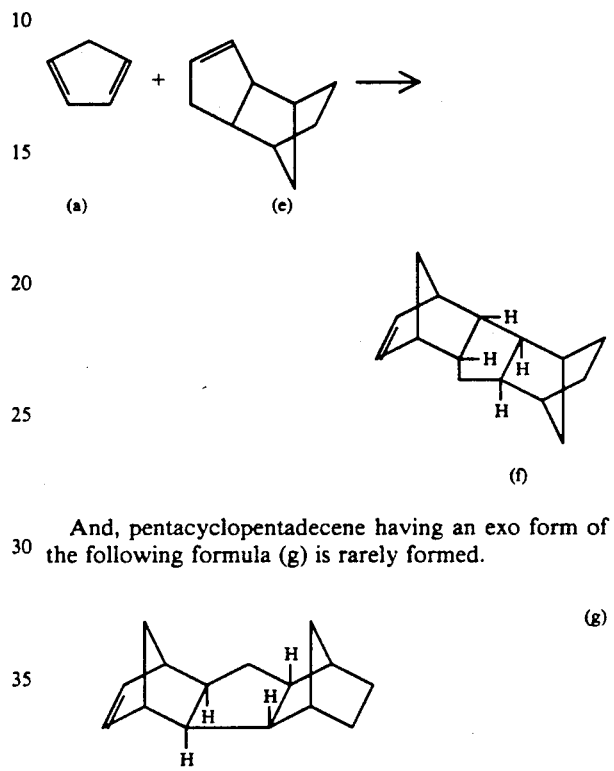

And, pentacyclopentadecene having an exo form of the following formula (g) is rarely formed.

The present applicants have made a diligent study to further improve heat resistance and mechanical strength of the above random copolymer of a cycloolefin and ethylene, and found the following. That is, when an isomer mixture containing a larger amount of a cycloolefin having an exo form (sometimes called "exo-form cycloolefin" hereinbelow) is used as a cycloolefin, the resultant random copolymer has remarkably improved heat resistance and mechanical strength. And, the present applicants have found an industrially advantageous process for isomerization for the production of such an isomer mixture containing a large amount of an exo form cycloolefin.

SUMMARY OF THE INVENTION

It is an object of this invention to provide a process for the isomerization of a cycloolefin having an endo form (sometimes called "endo-form cycloolefin" hereinbelow) to a cycloolefin having an exo form.

It is another object of this invention to provide a process for the production of an isomer mixture rich with a cycloolefin having an exo form from an isomer mixture poor with such a cycloolefin having an exo form under an isomerization reaction.

It is further another object of this invention to provide a compositionally novel isomer mixture containing up to 80 mol % of an endo-form cycloolefin and at least 20 mol % of an exo-form cycloolefin.

It is still further another object of this invention to provide a random copolymer produced from the above compositionally novel isomer mixture and ethylene and having excellent heat resistance and mechanical strength, and a process for the production of such a random copolymer.

The other objects and advantages of this invention will be apparent from the following description.

The above objects and advantages of this invention are achieved first by a process for the isomerization of a cycloolefin from an endo form to an exo form which comprises isomerizing an endo-form cycloolefin of the following formula (I)

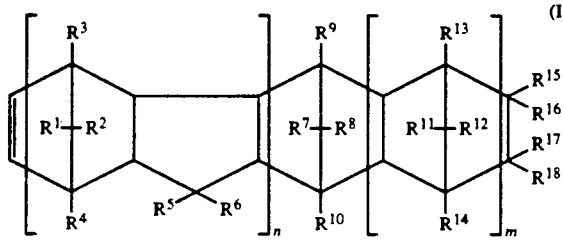

(I)

wherein $R^1$ to $R^{14}$ are independently a hydrogen atom, a halogen atom or a hydrocarbon group, $R^{15}$ to $R^{18}$ are independently a hydrogen atom, a halogen atom or a hydrocarbon group, or $R^{15}$ or $R^{16}$ and $R^{17}$ or $R^{18}$ may be bonded to each other to form a monocyclic or polycyclic group, or $R^{15}$ and $R^{16}$ or $R^{17}$ and $R^{18}$ may together form an alkylidene group, n is 0 or 1, and m is 0 or a positive integer, provided that m and n cannot be simultaneously zero, in the presence of a solid acid catalyst to convert its endo form into the corresponding exo form.

DETAILED DESCRIPTION OF THE INVENTION

Figure 1:
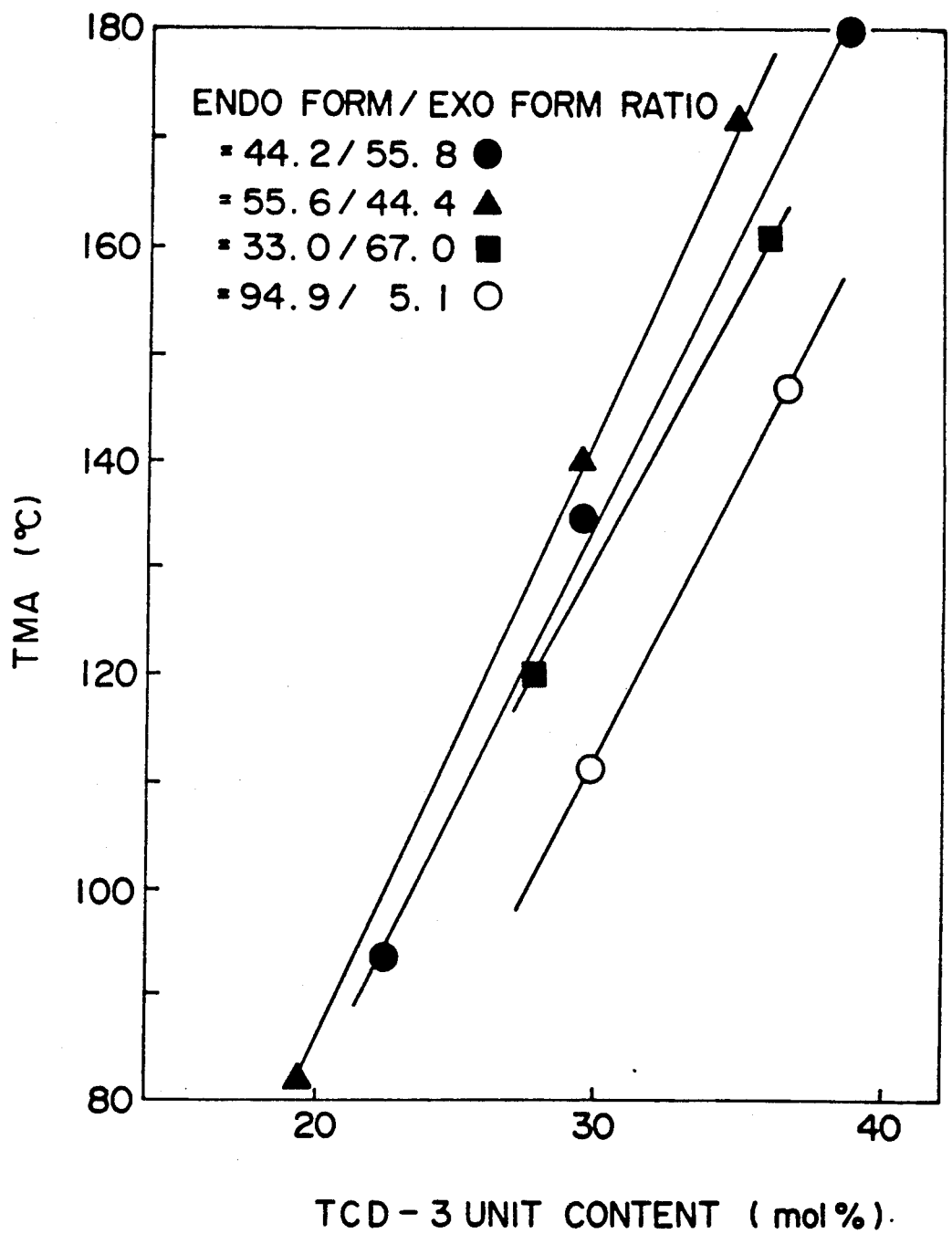
FIG. 1 shows a relationship between a content (mol %) of tetracyclododecene-3 in each of ethylenetetracyclododecene-3 copolymers obtained by copolymerization of ethylene with each of four tetracyclododecene-3 isomer mixtures having a different endo-form cycloolefin/exo-form cycloolefin ratio and a TMA softening temperature of each of the copolymers.

The starting material used in this invention is a cycloolefin having an endo form, and represented by the foregoing formula (I).

In the formula (I), each of $R^1$ to $R^{14}$, independently from each other, is a hydrogen atom, a halogen atom or a hydrocarbon group. Preferred examples of the halogen atom are fluorine, chlorine and bromine. Preferred examples of the hydrocarbon group are lower alkyl groups such as methyl, ethyl, n-propyl, iso-propyl, n-butyl, sec-butyl, iso-butyl and tert-butyl groups.

Further, in the formula (I), each of $R^{15}$ to $R^{18}$, independently from each other, is a hydrogen atom, a halogen atom or a hydrocarbon group. Examples of the halogen atom are as specified above. Preferred examples of the hydrocarbon group are alkyl groups such as methyl, ethyl, propyl, iso-propyl, n-butyl, iso-butyl, hexyl and stearyl groups, and cycloalkyl groups such as a cyclohexyl group.

$R^{15}$ or $R^{16}$ and $R^{17}$ or $R^{18}$ may be bonded to each other to form a monocyclic or polycyclic group, or $R^{15}$ and $R^{16}$ or $R^{17}$ and $R^{18}$ may form an alkylidene group together. As the monocyclic or polycyclic group, $R^{15}$ or $R^{16}$ and $R^{17}$ or $R^{18}$ may form, e.g. a cyclopentyl group, cyclopentenyl group, cyclohexyl group or the like together with carbon atoms to which $R^{15}$, $R^{16}$, $R^{17}$ and $R^{18}$ are bonded. And, preferred examples of the above alkylidene group are ethylidene, propylidene, and isopropylidene groups.

The "n" is 0 or 1, and the "m" is 0 or a positive integer, provided that n and m cannot be zero at the same time.

In the above formula (I), when n is 0 and m is 1, the above formula (I) is represented by the following formula (I-A)

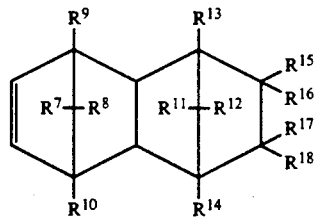

(I-A)

wherein $R^7$ to $R^{18}$ are as defined in the above formula (I).

And, when n is 1 and m is 0, the above formula (I) is represented by the following formula (I-B)

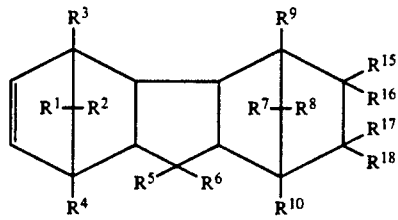

(I-B)

wherein $R^1$ to $R^{10}$ and $R^{15}$ to $R^{18}$ are as defined in the above formula (I).

Specific examples of the cycloolefin of the formula (I) (including the above formulae (I-A) and (I-B)) are preferably as follows:

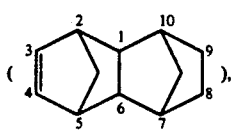

Tetracyclo[4,4,0,1$^{2,5}$,1$^{7,10}$]-3-dodecene
8-methyltetracyclo[4,4,0,1$^{2,5}$,1$^{7,10}$]-3-dodecene,
8-methyl-tetracyclo[4,4,0,1$^{2,5}$,1$^{7,10}$]-3-dodecene,
8-ethyltetracyclo[4,4,0,1$^{2,5}$,1$^{7,10}$]-3-dodecene,
8-propyltetracyclo[4,4,0,1$^{2,5}$,1$^{7,10}$]-3-dodecene,
8-hexyltetracyclo[4,4,0,1$^{2,5}$,1$^{7,10}$]-3-dodecene,
8-stearyltetracyclo[4,4,0,1$^{2,5}$,1$^{7,10}$]-3-dodecene,
8,9-dimethyltetracyclo[4,4,0,1$^{2,5}$,1$^{7,10}$]-3-dodecene,
8-methyl-9-ethyltetracyclo[4,4,0,1$^{2,5}$,1$^{7,10}$]-3-dodecene,
8-chlorotetracyclo[4,4,0,1$^{2,5}$,1$^{7,10}$]-3-dodecene,
8-bromotetracyclo[4,4,0,1$^{2,5}$,1$^{7,10}$]-3-dodecene, 8-fluorotetracyclo[4,4,0,1$^{2,5}$,1$^{7,10}$]-3-dodecene,
8,9-dichlorotetracyclo[4,4,0,1$^{2,5}$,1$^{7,10}$]-3-dodecene,
8-cyclohexyltetracyclo[4,4,0,1$^{2,5}$,1$^{7,10}$]-3-dodecene,
8-isobutyltetracyclo[4,4,0,1$^{2,5}$,1$^{7,10}$]-3-dodecene,
8-butyltetracyclo[4,4,0,1$^{2,5}$,1$^{7,10}$]-3-dodecene,
8-ethylidenetetracyclo[4,4,0,1$^{2,5}$,1$^{7,10}$]-3-dodecene,
8-ethylidene-9-methyltetracyclo[4,4,0,1$^{2,5}$,1$^{7,10}$]-3-dodecene,
8-ethylidene-9-ethyltetracyclo[4,4,0,1$^{2,5}$,1$^{7,10}$]-3-dodecene,
8-ethylidene-9-isopropyl-tetracyclo[4,4,0,1$^{2,5}$,1$^{7,10}$]-3-dodecene,
8-ethylidene-9-butyl-tetracyclo[4,4,0,1$^{2,5}$,1$^{7,10}$]-3-dodecene,
8-n-propylidene-tetracyclo[4,4,0,1$^{2,5}$,1$^{7,10}$]-3-dodecene,
8-n-propylidene-9-methyltetracyclo[4,4,0,1$^{2,5}$,1$^{7,10}$]-3-dodecene,
8-n-propylidene-9-ethyltetracyclo[4,4,0,1$^{2,5}$,1$^{7,10}$]-3-dodecene,
8-n-propylidene-9-isopropyltetracyclo[4,4,0,1$^{2,5}$,1$^{7,10}$]-3-dodecene,
8-n-propylidene-9-butyltetracyclo[4,4,0,1$^{2,5}$,1$^{7,10}$]-3-dodecene,
8-isopropylidenetetracyclo[4,4,0,1$^{2,5}$,1$^{7,10}$]-3-dodecene,
8-isopropylidene-9-methyltetracyclo[4,4,0,1$^{2,5}$,1$^{7,10}$]-3-dodecene,
8-isopropylidene-9-ethyltetracyclo[4,4,0,1$^{2,5}$,1$^{7,10}$]-3-dodecene,
8-isopropylidene-9-isopropyltetracyclo[4,4,0,1$^{2,5}$,1$^{7,10}$]-3-dodecene,
8-isopropylidene-9-butyltetracyclo[4,4,0,1$^{2,5}$,1$^{7,10}$]-3-dodecene,
5,10-dimethyltetracyclo[4,4,0,1$^{2,5}$,1$^{7,10}$]-3-dodecene,
2,10-dimethyltetracyclo[4,4,0,1$^{2,5}$,1$^{7,10}$]-3-dodecene,
11,12-dimethyltetracyclo[4,4,0,1$^{2,5}$,1$^{7,10}$]-3-dodecene,
2,7,9-trimethyltetracyclo[4,4,0,1$^{2,5}$,1$^{7,10}$]-3-dodecene,
9-ethyl-2,7-dimethyltetracyclo[4,4,0,1$^{2,5}$,1$^{7,10}$]-3-dodecene,
9-isobutyl-2,7-dimethyltetracyclo[4,4,0,1$^{2,5}$,1$^{7,10}$]-3-dodecene,
9,11,12-trimethyltetracyclo[4,4,0,1$^{2,5}$,1$^{7,10}$]-3-dodecene,
9-ethyl-11,12-dimethyltetracyclo[4,4,0,1$^{2,5}$,1$^{7,10}$]-3-dodecene,
9-isobutyl-11,12-dimethyltetracyclo[4,4,0,1$^{2,5}$,1$^{7,10}$]-3-dodecene,
5,8,9,10-tetramethyltetracyclo[4,4,0,1$^{2,5}$,1$^{7,10}$]-3-dodecene;
pentacyclo[6,5,1,1$^{3,6}$,0$^{2,7}$,0$^{9,13}$]-4-pentadecene

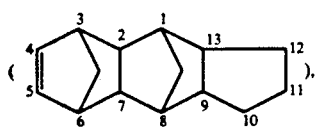

1,3-dimethyl-pentacyclo[6,5,1,1$^{3,6}$,0$^{2,7}$,0$^{9,13}$]-4-pentadecene,
1,6-dimethyl-pentacyclo[6,5,1,1$^{3,6}$,0$^{2,7}$,0$^{9,13}$]-4-pentadecene,
14,15-dimethyl-pentacyclo[6,5,1,1$^{3,6}$,0$^{2,7}$,0$^{9,13}$]-4-pentadecene,
pentacyclo[6,6,1,1$^{3,6}$,0$^{2,7}$,0$^{9,13}$]-4-pentadecene;
1,3-dimethyl-pentacyclo[6,6,1,1$^{3,6}$,0$^{2,7}$,0$^{9,14}$]-4-hexadecene

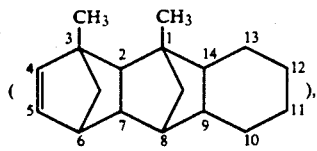

1,6-dimethyl-pentacyclo[6,6,1,1$^{3,6}$,0$^{2,7}$,0$^{9,14}$]-4-hexadecene,
15,16-dimethyl-pentacyclo[6,6,1,1$^{3,6}$,0$^{2,7}$,0$^{9,14}$]-4-hexadecene;
pentacyclo[6,5,1,1$^{3,6}$,0$^{2,7}$,0$^{9,13}$]-pentadecadiene-4,10

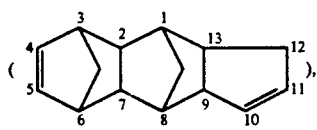

pentacyclo[4,7,0,1$^{2,5}$,1$^{9,12}$,0$^{8,13}$]-3-pentadecene

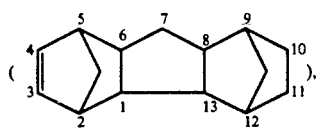

methyl-substituted pentacyclo[4,7,0,1$^{2,5}$,1$^{9,12}$,0$^{8,13}$]-3-pentadecene,
dimethyl-substituted pentacyclo[4,7,0,1$^{2,5}$,1$^{9,12}$,0$^{8,13}$]-3-pentadecene,
trimethyl-substituted pentacyclo[4,7,0,1$^{2,5}$,1$^{9,12}$,0$^{8,13}$]-3-pentadecene;
heptacyclo-[7,8,0,1$^{3,6}$,1$^{10,17}$,1$^{12,15}$,0$^{1,9}$,0$^{2,7}$,0$^{11,16}$]-4-eicosene

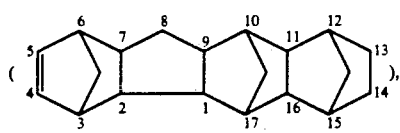

trimethyl-substituted heptacyclo[7,8,0,1$^{3,6}$,1$^{10,17}$,1$^{12,15}$,0$^{1,9}$,0$^{2,7}$,0$^{11,16}$]-4-eicosene,
tetramethyl-substituted heptacyclo[7,8,0,1$^{3,6}$,1$^{10,17}$,1$^{12,15}$,0$^{1,9}$,0$^{2,7}$,0$^{11,16}$]-4-eicosene,
methyl-substituted heptacyclo[7,8,0,1$^{3,6}$,1$^{10,17}$,1$^{12,15}$,0$^{1,9}$,0$^{2,7}$,0$^{11,16}$]-4-eicosene,
dimethyl-substituted heptacyclo[7,8,0,1$^{3,6}$,1$^{10,17}$,1$^{12,15}$,0$^{1,9}$,0$^{2,7}$,0$^{11,16}$]-4-eicosene;
and
nonacyclo[9,10,1,1$^{4,7}$,1$^{13,20}$,1$^{15,18}$,0$^{2,10}$,0$^{3,8}$,0$^{12,21}$,0$^{14,19}$]-5-pentacosene

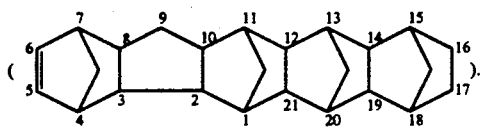

The endo form of a cycloolefin, when it is, e.g. tetracyclo[4,4,0,1$^{2,5}$,1$^{7,10}$]-3-dodecene, is represented by the following formula (c) as described above.

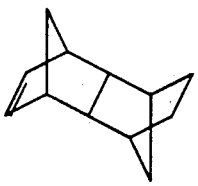

And, the end form of a cycloolefin, when it is e.g. pentacyclo-[4,7,0,1$^{2,5}$,0$^{8,13}$,1$^{9,12}$]-3-pentadecene, is represented by the following formula (f) as described above.

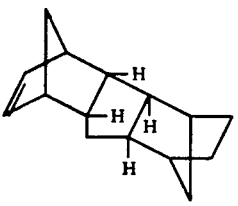

The stereostructure of the endo form of a cycloolefin is believed to be clear on the basis of the above-specified formulae.

In the process of this invention, the above-described cycloolefins having an endo form are converted into cycloolefins having the corresponding exo form by isomerization in the presence of a solid acid catalyst.

The stereostructure of the exo form cycloolefin is believed to be clear on the basis of the following formulae. That is, for example, the exo form corresponding to the endo form of the formula (c) is represented by the following formula (d),

and the exo form corresponding to the endo form of the formula (f) is represented by the following formula (g).

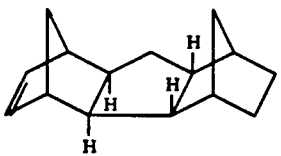

In the process of this invention, preferred as a solid acid catalyst are oxides or sulfides of metals belonging to the groups 3 to 8 of the periodic table or organic solid acids. Preferred examples of the oxides and sulfides are those of Al, Si, P, Ti, V, Cr, Mo, W, Mn, Fe or Co. Specific examples of such oxides and sulfides are silica-alumia (composed mainly of $Al_2O_3$ and $SiO_2$), alumina (composed mainly of $Al_2O_3$), zeolite (composed mainly of $Na_2O$, $Al_2O_3$ and $SiO_2$), activated clay, $Cr_2O_3$, $P_2O_3$, $TiO_2$, $Al_2O_3$—$xCr_2O_3$, $Al_2O_3$—CoO, $Al_2O_3$—MnO, $Cr_2O_3$—$Fe_2O_3$, MoS, $MoS_2$, $CrO_3$, $CrO_2Cl_2$, $MoO_3$, $V_2O_3$, and $WO_2Cl_2$.

As is clear from the above-specified compounds, the scope of the oxides and sulfides used in this invention also include those containing an alkaline metal or a halogen atom.

Preferred as the organic solid acid are sulfonic acid group-containing polymers, which are commercially available, e.g. under the trade names of Amberlist 15, Amberlite XE-284 and Nafion-H.

The isomerization reaction is carried out by bringing a cycloolefin having an endo form into contact with a solid acid catalyst. In this case, the cycloolefin may be directly brought into contact with a solid acid catalyst, or may be brought into contact with a solid acid catalyst in the presence of an organic solvent.

Specific examples of the organic solvent are cyclohexane, decalin, hexane, benzene, carbon tetrachloride, 1,2-dichloroethane, and the like.

The isomerization reaction is carried out advantageously at $-5°$ to $150°$ C., preferably at $0°$ to $50°$ C. The reaction time depends on a reaction temperature and a concentration of the cycloolefin. However, it is preferably 0.5 to 200 hours, more preferably 1 to 100 hours.

The reaction may be carried out by a batch method or a continuous method. The reaction according to a batch method is specifically carried out, e.g. as follows.

A reaction vessel equipped with a stirrer is charged with predetermined amounts of a cycloolefin, an organic solvent as required, and a solid acid, and the resultant mixture is stirred at a predetermined temperature for a predetermined period of time. Thereafter, the resultant reaction mixture is separated into a solid phase and a liquid phase by filtration, and further, the cycloolefin and the organic solvent in the liquid phase are separated, e.g. by distillation.

The reaction is also carried out according to the following continuous method.

(i) The same apparatus as that used in the above batch method is continuously charged with a cycloolefin or a cycloolefin diluted with an organic solvent to bring it into contact with a solid acid catalyst present in the apparatus, and the cycloolefin or the cycloolefin diluted with an organic solvent is continuously withdrawn, or (ii) a cycloolefin or a cycloolefin diluted with an organic solvent is charged into one end of a column packed with a solid acid catalyst, and continuously withdrawn from the other end.

In both of the above methods (i) and (ii), a distillation method is usable to separate the cycloolefin from the organic solvent after the cycloolefin is brought into contact with a solid acid catalyst.

According to the above isomerization process of this invention, a cycloolefin can be converted from an endo form to an exo form. The structures of the endo form and the exo form and the molar ratio of the endo and exo forms in an isomer mixture can be determined by measuring $^1$H-NMR or $^{13}$C-NMR.

According to this invention, there is further provided a process for the production of an isomer mixture rich with an exo-form cycloolefin, which comprises subjecting an isomer mixture rich with an endo-form cycloolefin of the formula (I) (including the formulae (I-A) and (I-B)) to an isomerization reaction in the presence of a solid acid catalyst by using the above isomerization process.

In the above process, the isomer mixture rich with an endo-form cycloolefin preferably comprises, based on the total of endo-form and exo-form cycloolefins, at least 85 mol %, preferably at least 90 mol %, particularly preferably at least 94 mol % of an endo-form cycloolefin and up to 15 mol %, preferably up to 10 mol %, particularly preferably up to 6 mol % of an exo-form cycloolefin. Further, the resultant isomer mixture rich with the exo-form preferably comprises, based on the total of endo-form and exo-form cycloolefins, up to 80 mol % of an endo-form cycloolefin and at least 20 mol % of an exo-form cycloolefin. More preferably, the isomer mixture comprises 70 to 5 mol % of an endo-form cycloolefin and 30 to 95 mol % of an exo-form cycloolefin.

The above isomer mixture rich with an endo-form cycloolefin (starting material) can be easily prepared from the foregoing starting substance by a Diels-Alder reaction, whereas the isomer mixture rich with an exo-form cycloolefin can be provided according to the above process of this invention for the first time.

Therefore, according to this invention, there is further provided an isomer mixture of a cycloolefin of the formula (I) (including (I-A) and (I-B)), i.e. an isomer mixture comprising up to 80 mol % of an endo-form cycloolefin and at least 20 mol % of an exo-form cycloolefin, preferably, an isomer mixture comprising 70 to 5 mol % of an endo-form cycloolefin and 30 to 95 mol % of an exo-form cycloolefin.

When the isomer mixture of this invention is copolymerized with ethylene, it gives a novel random copolymer having excellent heat resistance and mechanical strength.

The novel random copolymer of this invention has the following features:

(1) It is a random copolymer of an isomer mixture of up to 80 mol % of an endo-form cycloolefin of the formula (I) (including the formulae (I-A) and (I-B)) and at least 20 mol % of an exo-form cycloolefin thereof and ethylene.

(2) It comprises, based on the total of polymer units derived from the cycloolefin and polymer units derived from ethylene, 10 to 90 mol % of the polymer units derived from the cycloolefin and 90 to 10 mol % of the polymer units derived from ethylene.

(3) The polymer units derived from the cycloolefin are represented by the following formula (II)

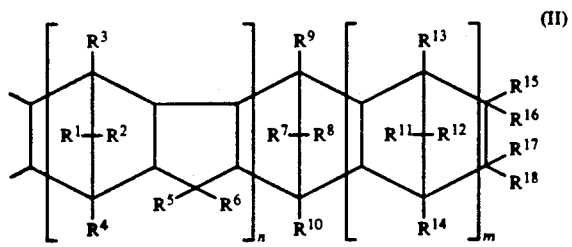

wherein $R^1$ to $R^{18}$, n and m are as defined as above.

(4) It has an intrinsic viscosity [η], measured in decalin at 135° C., of 0.05 to 10 dl/g.

In the above random copolymer, when a cycloolefin of the formula (I-A) is used as an olefin of the formula (I), the polymer unit of the formula (II) is represented by the following formula (II-A)

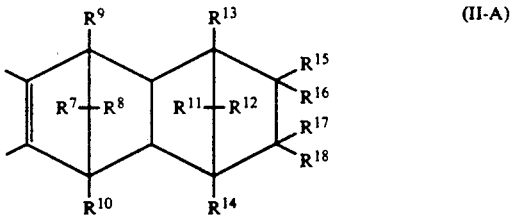

wherein $R^7$ to $R^{18}$ are as defined above.

And, when a cycloolefin of the formula (I-B) is similarly used, the polymer unit of the formula (II) is represented by the following formula (II-B).

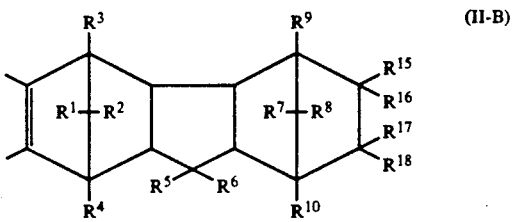

wherein $R^1$ to $R^{10}$ and $R^{15}$ to $R^{18}$ are as defined above.

According to this invention, the above random copolymer can be produced by copolymerizing the above isomer mixture and ethylene in a hydrocarbon solvent or without any hydrocarbon solvent in the presence of a catalyst which is composed of a vanadium compound and an organoaluminum and soluble in the hydrocarbon solvent or a cycloolefin of the isomer mixture.

Such a random-copolymer and the process for the production thereof will be explained in detail below.

In the production of the cycloolefin random copolymer, the copolymerization reaction between ethylene and the cycloolefin is carried out in a hydrocarbon solvent or without any hydrocarbon solvent. Examples of the hydrocarbon solvent are aliphatic hydrocarbons such as hexane, heptane, octane and kerosine; alicyclic hydrocarbons such as cyclohexane and methylcyclohexane; and aromatic hydrocarbons such as benzene, toluene and xylene. These solvents may be used alone or in combination.

The vanadium compound is specifically a compound of the general formula $VO(OR)_a X_b$ or $V(OR)_c X_d$ wherein R represents a hydrocarbon group, X represents a halogen atom, a and b are defined by $0 \leq a \leq 3$, $0 \leq b \leq 3$, and $2 \leq a+b \leq 3$, and c and d are defined by $0 \leq c \leq 4$, $0 \leq d \leq 4$, and $3 \leq c+d \leq 4$, or an adduct of this compound with an electron donor.

Specific examples of the vanadium compounds are $VOCl_3$, $VO(OC_2H_5)Cl_2$, $VO(OC_2H_5)_2Cl$, $VO(O-i-so-C_3H_7)Cl_2$, $VO(O-n-C_4H_9)Cl_2$, $VO(OC_2H_5)_3$, $VOBr_2$, $VCl_4$, $VOCl_2$, $VO(O-n-C_4H_9)_3$ and $VCl_3 \cdot 2(CO_8H_{17}OH)$.

Further, examples of the electron donor which may be used to prepare the soluble vanadium catalyst component are oxygen-containing electron donors such as an alcohol, phenols, a ketone, an aldehyde, a carboxylic acid, an ester of an organic or inorganic acid, an ether, an acid amide, an anhydride and an alkoxysilane; and nitrogen-containing electron donors such as ammonia, an amine, a nitrile, and isocyanate. Specific examples of the electron donors are alcohols having 1 to 18 carbon atoms such as methanol, ethanol, propanol, pentanol, hexanol, octanol, dodecanol, octadecyl alcohol, oleyl alcohol, benzyl alcohol, phenylethyl alcohol, cumyl alcohol, isopropyl alcohol and isopropylbenzyl alcohol; phenols having 6 to 20 carbon atoms, (which may have a lower alkyl group as a substituent), such as phenol, cresol, xylenol, ethylphenol, propylphenol, nonylphenol, cumylphenol and naphthol; ketones having 3 to 15 carbon atoms such as acetone, methyl ethyl ketone, methyl isobutyl ketone, acetophenone, benzophenone and benzoquinone; aldehydes having 2 to 15 carbon atoms such as acetaldehyde, propionaldehyde, octylaldehyde, benzaldehyde, tolualdehyde and naphthaldehyde; organic acid esters having 2 to 30 carbon atoms such as methyl formate, methyl acetate, ethyl acetate, vinyl acetate, propyl acetate, octyl acetate, cyclohexyl acetate, ethyl propionate, methyl butyrate, ethyl valerate, methyl chloroacetate, ethyl dichloroacetate, methyl methacrylate, ethyl crotonate, ethyl cyclohexanecarboxylate, methyl benzoate, ethyl benzoate, propyl benzoate, butyl benzoate, octyl benzoate, cyclohexyl benzoate, phenyl benzoate, benzyl benzoate, methyl toluylate, ethyl toluylate, amyl toluylate, ethyl ethylbenzoate, methyl anisate, n-butyl maleate, diisobutyl methylmalonate, di-n-hexyl cyclohexenecarboxylate, diethyl ester of Nadic acid, diisopropyl tetrahydrophthalate, diethyl phthalate, diisobutyl phthalate, di-n-butyl phthalate, di-2-ethylhexyl phthalate, γ-butyrolactone, δ-valerolactone, coumarin, phthalide and ethylene carbonate; acid halides having 2 to 15 carbon atoms such as acetyl chloride, benzoyl chloride, toluic acid chloride and anisic acid chloride; ethers having 2 to 20 carbon atoms such as methyl ether, ethyl ether, isopropyl ether, butyl ether, amyl ether, tetrahydrofuran, anisole and diphenyl ether; acid amides such as acetic amide, benzoic amide and toluic amide; amines such as methyamine, ethylamine, diethylamine, tributylamine, piperidine, tribenzylamine, aniline, pyridine, picoline and tetramethylenediamine; nitriles such as acetonitrile, benzonitrile and tolunitrile; and alkoxysilanes such as ethyl silicate and diphenylmethoxysilane. These electron donors may be used in combination.

The organoaluminum compound as a component of the catalyst is a compound having at least one Al-carbon bond in the molecule. Examples of the organoaluminum compound are as follows.

(i) organoaluminum compounds of the general formula

wherein $R^1$ and $R^2$, same or different, each independently represent a hydrocarbon group having usually 1 to 15 carbon atoms, preferably 1 to 4 carbon atoms, X represents halogen, and m, n, p and q are defined by $0 \leq m \leq 3$, $0 \leq n \leq 3$, $0 \leq p \leq 3$, $0 \leq q \leq 3$ and $m+n+p+q=3$, and (ii) complex ion alkyl compounds, formed from a metal belonging to the group 1 of the periodic table and aluminum, of the general formula

wherein $M^1$ is Li, Na or K, and $R^1$ has the same meaning as above.

Examples of the organoaluminum compounds (i) are as follows.

Compounds of the formula $R^1_mAl(OR^2)_{3-m}$ wherein $R^1$ and $R^2$ have the same meanings as above, and m is defined preferably by $1.5 \leq m < 3$.

Compounds of the formula $R^1_mAlX_{3-m}$ wherein $R^1$ has the same meaning as above, X represents halogen, and m is defined preferably by $0 < m < 3$.

Compounds of the formula $R^1_mAlH_{3-m}$ wherein $R^1$ has the same meaning as above, and m is defined preferably by $2 \leq m < 3$.

Compounds of the formula $R^1_mAl(OR^2)_nX_q$ wherein $R^1$ and $R^2$ have the same meaning as above, X represents halogen, and m, n and q are defined by $0 < m \leq 3$, $0 \leq n < 3$, $0 \leq q < 3$ and $m+n+q=3$.

Specific examples of the organoaluminum compounds (i) are trialkylaluminum such as triethylaluminum and tributylaluminum; trialkenyl aluminum such as triisopropenylaluminum; dialkylaluminum alkoxides such as diethylaluminum ethoxide and dibutylaluminum butoxide; partially alkoxylated alkylaluminum having an average composition of the formula $R^1_{2.5}Al(OR^2)_{0.5}$ and alkylaluminum sesquialkoxides such as ethylaluminum sesquietoxide and butylaluminum sesquibutoxie; dialkylaluminum halides such as diethylaluminum chloride, dibutylaluminum chloride and diethylaluminum bromide; alkylaluminum sesquihalides such as ethylaluminum sesquichloride, butylaluminum sesquichloride and ethylaluminum sesquibromide; partially halogenated alkylaluminum such as ethylaluminum dichloride, propylaluminum dichloride, and butylaluminum dibromide; partially hydrogenated alkylaluminum such as dialkylaluminum hydrides, e.g. diethylaluminum hydride and dibutylaluminum hydride and alkylaluminum dihydrides, e.g. ethylaluminum dihydride and propylaluminum dihydrides; and partially alkoxylated and halogenated alkylaluminum such as ethylaluminum ethoxychloride, butylaluminum butoxychloride and ethylaluminum etoxybromide. Further, organoaluminum compounds which are similar to the compounds (i), e.g. organoaluminum compounds in which at least two aluminum atoms are bonded to each other through an oxygen or nitrogen atom are also usable. Specific examples of such compounds are $(C_2H_5)_2AlOAl(C_2H_5)_2$, $(C_4H_9)_2AlOAl(C_4H_9)_2$, and

Examples of the organoaluminum compounds (ii) are $LiAl(C_2H_5)_4$ and $LiAl(C_7H_{15})_4$. Of these compounds, alkylaluminum halides and alkylaluminum dihalides or mixtures of these are preferred.

When the cycloolefinic random copolymer is produced, it is preferable to carry out a copolymerization reaction of ethylene with a cycloolefin by a continuous method. And, in this case, the concentration of the soluble vanadium compound to be fed in the polymerization reaction system is usually not more than 10 times, preferably 1 to 7 times, more preferably 1 to 5 times as high as the concentration of the soluble vanadium compound in the polymerization reaction system.

The ratio of aluminum atoms to vanadium atoms (Al/V) in the polymerization reaction system is not less than 2, preferably 2 to 50, particularly preferably 3 to 20.

The soluble vanadium compound and the organoaluminum compound are usually charged to the reaction system after they are respectively diluted with the above-specified hydrocarbon solvent or cycloolefin. And, the soluble vanadium compound is preferably diluted to the above concentration before it is charged, and the organoaluminum compound is also diluted to a concentration in the range of, e.g. not more than 50 times as high as the concentration thereof in the polymerization reaction system, and then charged to the polymerization reaction system.

When the cycloolefin random copolymer is produced, the concentration, as a vanadium atom, of the soluble vanadium compound in the copolymerization system is usually 0.01 to 5 gram-atom/l, preferably 0.05 to 3 gram-atom/l.

The copolymerization reaction of ethylene with a cycloolefin is carried out at a temperature between −50° C. and 100° C., preferably between −30° C. and 80° C., more preferably between −20° C. and 60° C.

The reaction time for the above copolymerization reaction (or an average residence time of a polymerization reaction mixture in the case of a continuous polymerization) differs depending upon polymerization materials, concentration of catalyst components and temperatures. The reaction time is usually 5 minutes to 5 hours, preferably 10 minutes to 3 hours. The pressure for the copolymerization reaction is usually more than 0 and up to 50 kg/cm², preferably more than 0 and up to 20 kg/cm².

When the cycloolefin random copolymer is produced, the molar ratio of ethylene and cycloolefin to be fed is usually 90/10 to 10/90, preferably 85/15 to 40/60. The ethylene unit/cycloolefin unit constitutional ratio in the resulting ethylene/cycloolefin copolymer is usually 90/10 to 40/60, preferably 85/15 to 50/50.

The above cycloolefinic random copolymer may contain other copolymerizable monomers, e.g. norbornenes other than the cycloolefin of the formula (I) or α-olefins other than ethylene in such an amount that does not impair the object of this invention or not more than 15 mol % based on the total polymer units.

The above copolymerization reaction of ethylene with a cycloolefin gives a solution of a cycloolefin random copolymer in the hydrocarbon solvent or a solution thereof in an unreacted cycloolefin. The concentration of the cycloolefinic random copolymer in such a solution is usually 2.0 to 200 g/l (g-polymer/l-polymerization liquid), preferably 40 to 100 g/l. The solution also contains the soluble vanadium compound component and the organoaluminum compound components of the catalyst.

The above solution of the cycloolefin random copolymer is usually subjected to a series of treatments starting with deashing and finishing with pelleting, whereby pellets of the cycloolefin random copolymer are obtained.

In the above cycloolefin random copolymer, the structural unit derived from the cycloolefin of the formula (I) is present in a structure shown in the following formula (II)

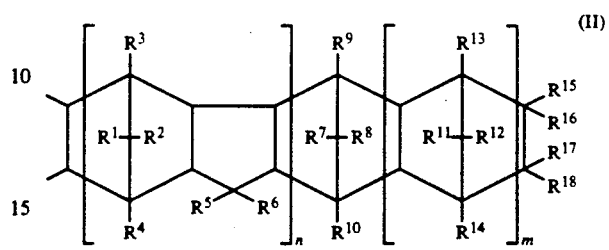

wherein $R^1$ to $R^{18}$, n and m are as defined as above.

The above ethylene-cycloolefin random copolymer preferably has an intrinsic viscosity [η], measured in Decalin (decahydronaphthalene) at 135° C., of 0.05 to 10 dl/g.

The above random copolymer produced from the isomer mixture of this invention has a high glass transition point (Tg) or superior heat resistance and a high flexural modulus (FM) or superior mechanical strength as compared with any conventional cycloolefin random copolymer obtained by copolymerization of ethylene with an isomer mixture containing 85 mol % or more, 90 mol % or more, in many cases, or 94 mol % or more, further in many cases, of an endo-form cycloolefin of the formula (I) (naturally when the comparison is made on the same composition of ethylene and a cycloolefin). Therefore, when the isomer mixture according to this invention is used, it is possible to reduce the amount of expensive tetracyclododecenes and obtain a copolymer having an identical glass transition point (Tg) or a flexural modulus to that of any conventional copolymer.

This invention will be explained below by reference to Examples, which however shall not limit this invention.

QUANTITATIVE DETERMINATION METHOD (a) The endo-form cycloolefin/exo-form cycloolefin molar ratio of an isomer mixture of tetracyclo[4,4,0,1²,⁵,1⁷,¹⁰]-3-dodecene (to be abbreviated as TCD-3 hereinafter) was calculated as follows. TCD-3 was subjected to ¹H-NMR (in CDCl₃, room temperature, TMS standard), and an integration strength ratio of olefin proton absorption peaks in the resultant spectrum was used as a basis for the calculation. Table 1 shows chemical shifts of olefin protons obtained by measurement of ¹H-NMR of tetracyclo-[4,4,0,1²,⁵,1⁷,¹⁰]-3-dodecene.

Table 1 also shows chemical shifts of carbons obtained by measurement of ¹³C-NMR of tetracyclo-[4,4,0,1²,⁵,1⁷,¹⁰]-3-dodecene.

TABLE 1

$^1$H-NMR and $^{13}$C-NMR chemical shifts of TCD-3 (monomer) (TMS standard)

(ppm)

| Structure | $^1$H-NMR olefin protons | $^{13}$C-NMR | | | | | | |
|---|---|---|---|---|---|---|---|---|
| | | h, i | l | g, j | k | a, f | b, e | c, d |
| (Endo form) | 6.1 (triplet) | 31.9 | 33.7 | 37.9 | 46.7 | 48.7 | 52.8 | 134.7 |
| (Exo form) | 5.9 (triplet) | 31.2 | 33.7 | 38.8 | 42.4 | 45.7 | 49.7 | 138.7 |

Measurement conditions: $^1$H-NMR in CDCl$_3$, room temperature
Measurement conditions: $^{13}$C-NMR in CDCl$_3$, room temperature Further, Table 2 shows chemical shifts of carbons obtained by measurement of $^{13}$C-NMR of a TCD-3 copolymer.

strength spectrum was used as a basis for the calculation. Table 3 shows chemical shifts of olefin protons obtained by measurement of $^1$H-NMR of PCPD.

TABLE 2

$^{13}$C-NMR chemical shifts in ethylene-TCD-3 copolymer (TMS standard)

δ(ppm)

| Structure | $^{13}$C-NMR | | | | | | |
|---|---|---|---|---|---|---|---|
| | h, i | l | g, j | k | a, f | b, e | c, d |
| (Endo form) | 31.7 | 35.2 | 36.9 | 36.6 36.8 | 50.8 | 45.5 49.0 | 39.0 41.0 |
| (Exo form) | 31.0 | 35.6 | 40.4 | 29.4 31.4 | 54.4 | 45.5 49.0 | 45.5 49.0 |

Measurement conditions: $^{13}$C-NMR in hexachloro-1,3-butadiene, 100° C.

(b) The endo-form cycloolefin/exo-form cycloolefin molar ratio of an isomer mixture of tetracyclo[4,7,0,1$^{2,5}$,1$^{9,12}$,0$^{8,3}$]-3-pentadecene (to be abbreviated as PCPD hereinafter) was calculated similarly as follows. PCPD was subjected to $^1$H-NMR (in CDCl$_3$, room temperature, TMS standard), and an integration Table 3 also shows chemical shifts of carbons obtained by measurement of $^{13}$C-NMR of PCPD.

Table 4 shows chemical shifts of carbons obtained by measurement of $^{13}$C-NMR of an ethylene-PCPD copolymer.

TABLE 3

$^1$H-NMR and $^{13}$C-NMR chemical shifts of PCPD (monomer) (TMS standard)

| Structure | $^1$H-NMR olefin protons | $^{13}$C-NMR δ(ppm) | | | | | | |
|---|---|---|---|---|---|---|---|---|
| (Endo form) | 6.1 (triplet) | g, k, j 30 | o 34 | i, l, h, m 38 | n 47.3 | a, f 49 | b, e 54 | c, d 135 |
| (Exo form) | 5.9 (triplet) | g, k, j 30 | o 34 | i, l, h, m 38 | n 43.5 | a, f 46 | b, e 50 | c, d 139 |

Measurement conditions: $^1$H-NMR in CDCl$_3$, room temperature
Measurement conditions: $^{13}$C-NMR in CDCl$_3$, room temperature

TABLE 4

$^{13}$C-NMR chemical shifts of PCPD unit in ethylene-PCPD copolymer (TMS standard)

| Structure | $^{13}$C-NMR δ(ppm) | | | | | | |
|---|---|---|---|---|---|---|---|
| (Endo form) | g, k, j 30 | o 34 | i, l, h, m 38 42 | n 37 | a, f 50 | [A] | c, d 39 41 |
| | | | | | | b, e 46 49 | |
| (Exo form) | g, k, j 30 | o 34 | i, l, h, m 38 42 | n 31 | a, f 55 | [B] | c, d 46 49 |

Measurement conditions: $^{13}$C-NMR in a C$_6$D$_6$, room temperature

METHOD OF MEASUREMENT OF SOFTENING TEMPERATURE

Copolymers prepared in Polymerization Examples and Comparative Polymerization Examples were respectively molded into sheet samples, and thermal deformation behavior thereof was measured by using a thermomechanical analyzer supplied by Du Pont. That is, the softening temperature is a temperature at which a quartz penetrator penetrated the sample 0.635 mm deep under a load of 49 g at a temperature elevation rate of 5° C./minute (the softening temperature is referred to as TMA softening temperature hereinafter).

METHOD OF MEASUREMENT OF FLEXURAL MODULUS

Measurement was made according to ASTM-D790 at 23° C.

METHOD OF MEASUREMENT OF INTRINSIC VISCOSITY

Measurement was made in Decalin (decahydronaphthalene) at 135° C.

REFERENTIAL EXAMPLE 1

Norbornene and cyclopentadiene were subjected to a Diels-Alder reaction according to a method described in Japanese Patent Publication No. 14910/1971 to synthesize tetracyclo[4,4,0,1$^{2,5}$,1$^{7,10}$]-3-dodecene

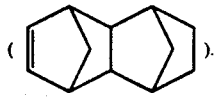

The resultant tetracyclododecene-3 compound had 94.9 mol % of an endo form and 5.1 mol % of an exo form as measured by $^1$H-NMR.

Table 5 shows the results.

REFERENTIAL EXAMPLE 2

5-Ethyl-2-norbornene and cyclopentadiene were subjected to a Diels-Alder reaction in the same way as in Referential Example 1 to synthesize 8-ethyl-tetracyclo[4,4,0,1$^{2,5}$,1$^{7,10}$]-3-dodexene

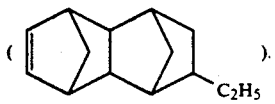

The resultant 8-ethyl-tetracyclo[4,4,0,1$^{2,5}$,1$^{7,10}$]-3-dodecene was measured by subjecting it to $^1$H-NMR to obtain an endo-form cycloolefin/exo-form cycloolefin molar ratio. This compound had 97.3 mol % of an endo-form cyclooefin and 2.7 mol % of an exo-form cycloolefin.

Table 5 shows the results.

EXAMPLE 1

A 30-liter reaction vessel equipped with stirrer and a reflux condenser was charged with 1 liter of the tetracyclo-[4,4,0,1$^{2,5}$,1$^{7,10}$]-3-dodecene (TCD-3) obtained in Referential Example 1 and 17 liters of cyclohexane, and the mixture was stirred. Twelve kilograms of zeolite (Zeolam F-9, trade name, a product of Tosoh Corporation, spherical forms, 1.8 to 2.4 mm$\phi$, Na$_2$O.Al$_2$O$_3$.2.5SiO$_2$) was added to the resultant solution, and the mixture was stirred at room temperature for 6 hours to carry out an isomerization reaction from an endo-form cyclooefin to an exo-form cycloolefin.

After the reaction, the reaction mixture was filtered to separate the catalyst, and the resultant solution of TCD-3 in cyclohexane was distilled under a reduced pressure (50 mmHg) to give isomerized TCD-3.

Analysis of the TCD-3 by $^1$H-NMR showed an endo-form cyclolefin/exo-form cycloolefin molar ratio of 44.2/55.8.

Table 5 shows the results.

EXAMPLE 2

Example 1 was repeated except that the reaction time was changed to 3 hours.

Table 5 shows the results.

EXAMPLE 3

Example 1 was repeated except that the catalyst was changed to silica-alumia (Sekado OW, a product of Shinagawa Refractories Co., Ltd., particulate, 0.5 to 2 mm$\phi$, Al$_2$O$_3$.mSiO$_2$.nH$_2$O+Al(OH)$_3$), that the amounts of the catalyst and cyclohexane were changed to 4.0 liters and 3 kg, respectively, and that the reaction time was changed to 96 hours.

Table 5 shows the results.

EXAMPLE 4

Example 1 was repeated except that the 8-ethyl-tetracyclo[4,4,0,1$^{2,5}$,1$^{7,10}$]-3-dodecene (8E-TCD-3 in short) obtained in Referential Example 2 was used.

Table 5 shows the results.

EXAMPLE 5

Example 4 was repeated except that the reaction time was changed to 3 hours.

Table 5 shows the results.

EXAMPLE 6

Example 4 was repeated except that the same silica-alumina as that used in Example 3 was used and that the reaction time was changed to 96 hours.

Table 5 shows the results.

TABLE 5

| Example No. | Abbreviation of TCDs | Conditions for isomerization reaction | | | | Composition ratio of isomers (%) Endo form/exo form |
|---|---|---|---|---|---|---|
| | | Cyclohexane (l) | TCDs (l) | Kind and amount of solid acid (kg) | Reaction time (hr) | |
| Referential Example 1 | TCD-3 | (before isomerization reaction) | | | | 94.9/5.1 |
| Example 1 | TCD-3 | 17.0 | 1.0 | zeolite[a] 6 | 6 | 44.2/55.8 |
| Example 2 | TCD-3 | 17.0 | 1.0 | zeolite[a] 6 | 3 | 55.6/44.4 |
| Example 3 | TCD-3 | 4.0 | 1.0 | silica-alumina[b] 3 | 96 | 33.0/67.0 |
| Referential Example 2 | 8E-TCD-3 | (before isomerization reaction) | | | | 97.3/2.7 |
| Example 4 | 8E-TCD-3 | 17.0 | 1.0 | zeolite[a] 6 | 6 | 50.1/49.9 |
| Example 5 | 8E-TCD-3 | 17.0 | 1.0 | zeolite[a] 6 | 3 | 39.7/60.3 |
| Example 6 | 8E-TCD-3 | 17.0 | 1.0 | silica-alumina[b] 6 | 96 | 7.2/92.8 |

[a] Zeolam F-9, a product of Tosoh Corporation; spherical, 1.8 to 2.4 mm$\phi$, composition formula Na$_2$O.Al$_2$O$_3$.2.5SiO$_2$
[b] Sekado OW, a product of Shinagawa Refractories Co., Ltd., spherical, 0.5 to 2 mm$\phi$, composition formula Al$_2$O$_3$.mSiO$_2$.nH$_2$O + Al(OH)$_3$

EXAMPLE 7

Polymerization EXAMPLE 1

A two-liter glass polymerizer having a stirrer was continuously charged, from its top, with a solution of the TCD-3 obtained in Example 1 in cyclohexane, a solution of VO(OC$_2$H$_5$)Cl$_2$ as a catalyst in cyclohexane and a solution of ethylaluminum sesquichloride (Al(C$_2$H$_5$)$_{1.5}$Cl$_{1.5}$) such that the concentrations thereof in the polymerizer were 60 g/l, 0.5 mmol/l and 4.0 mmol/l, respectively. And, the polymerizer was also charged from its top with ethylene at a rate of 15 liters/hour and hydrogen at a rate of 0.5 liter/hour. Separately, a reaction mixture was continuously withdrawn from the polymerizer bottom such that the total amount of a polymerization liquid in the polymerizer was 1 liter and that the residence time thereof was 0.5 hours.

The above polymerization reaction was carried out at 10° C. by circulating a refrigerant through a cooling jacket externally provided to the polymerizer.

Under the above copolymerization reaction conditions, a polymerization reaction mixture containing an ethylene-TCD-3 random copolymer was obtained. The polymerization reaction was stopped by adding a small amount of isopropyl alcohol to the polymerization liquid withdrawn from the polymerizer bottom. Then, the polymerization was charged into a mixer while the mixer containing acetone whose amount was about three times as large as the polymerization liquid was operated, whereby the copolymer was precipitated. The precipitated copolymer was recovered from the solution by filtration. The resultant copolymer was dispersed in acetone such that the concentration thereof was about 50 g/l, and the resultant mixture was further heat-treated at a boiling point of acetone. Thereafter, the copolymer was separated from the acetone by filtration, and dried under reduced pressure at 120° C. for 24 hours.

The resultant ethylene-TCD-3 copolymer was subjected to $^{13}$C-NMR to show that it had an ethylene content of 60.7 mol %. And, it had an intrinsic viscosity [η] of 0.37 dl/g and a TMA softening temperature of 180° C.

Figure 2:
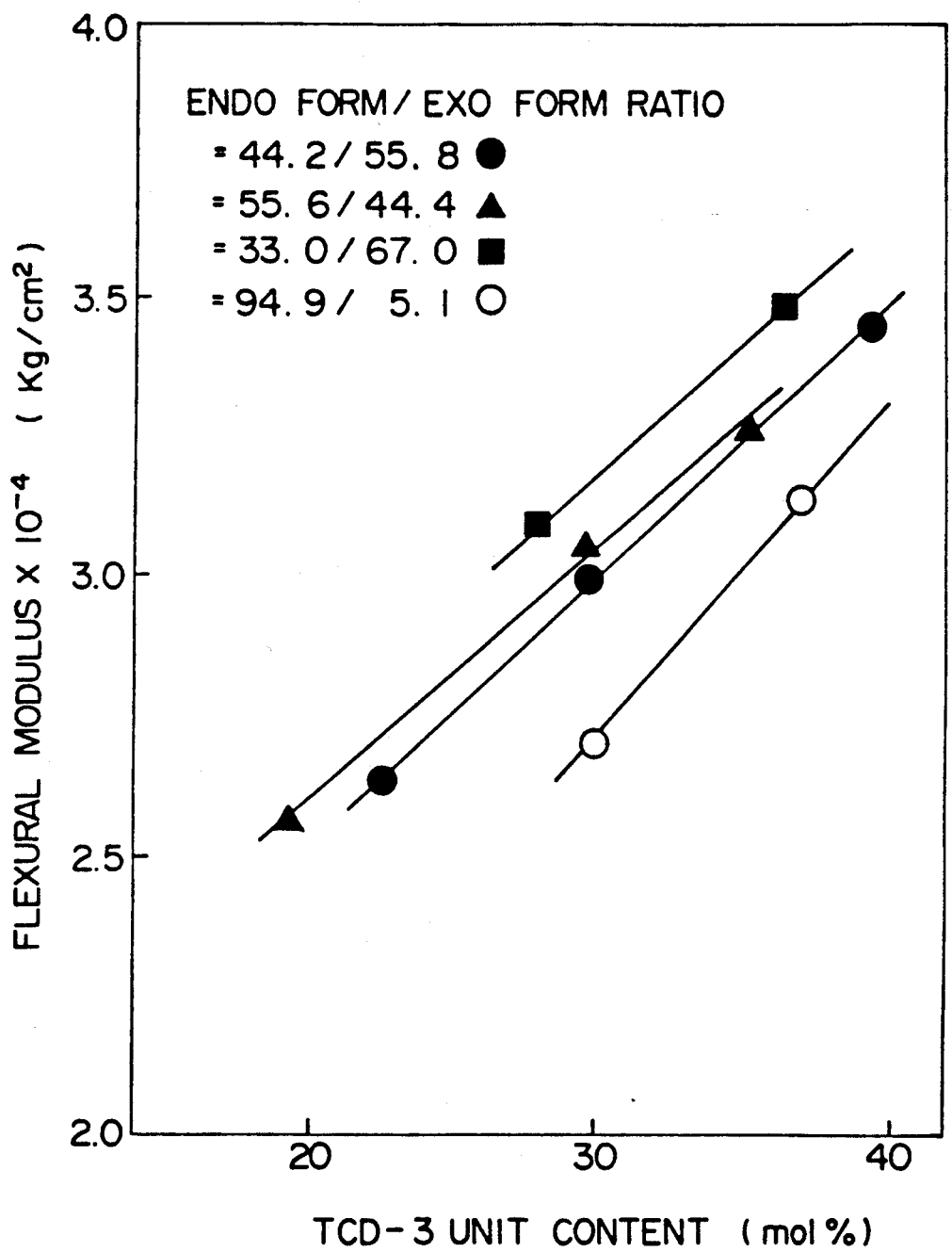
FIG. 2 shows a relationship between a content (mol %) of tetracyclododecene in the above ethylene/tetracyclododecene-3 copolymers and flexural modulus thereof.

Table 6 shows the results. Further, FIG. 1 shows the relationship between a tetracyclododecene-3 content (mol %) in the ethylene-tetracyclododecene-3 copolymer obtained as above and a softening temperature thereof. And, FIG. 2 shows the relationship between a tetracyclododecene content (mol %) of the copolymer above and flexural modulus thereof.

The above copolymer was also subjected to $^{13}$C-NMR to show that it had an endo form cycloolefin/exo form cycloolefin molar ratio of 41/59, and this value hardly changed from that obtained before the polymerization.

EXAMPLES 8-14

Polymerization EXAMPLES 2-8 and Comparative EXAMPLES 1 and 2 (Comparative Polymerization EXAMPLES 1 and 2)

Copolymerization of ethylene and tetracyclododecene was carried out in the same way as in Polymerization Example 1 by using materials (tetracyclododecene) shown in Table 6 under the conditions specified in Table 6.

Table 6 shows the results.

And, FIG. 1 shows the relationship between a tetracyclododecene-3 content (mol %) in the ethylenetetracyclododecene-3 copolymer obtained as above and a softening temperature thereof. And, FIG. 2 shows the relationship between a tetracyclododecene content (mol %) of the copolymer above and flexural modulus thereof.

TABLE 6

| Example No. | Polymerization Example No. | Amount of ethylene fed (l/hr) | TCDs Kind | TCDs Endo form/exo form ratio (mol %) | TCDs Amount (g/l) | H$_2$ Amount (l/hr) |
|---|---|---|---|---|---|---|
| Example 7 | Polymerization Example 1 | 15 | TCD-3 (Example 1) | 44.2/55.8 | 60 | 0.5 |
| Example 8 | Polymerization Example 2 | 30 | TCD-3 (Example 1) | 44.2/55.8 | 60 | 0.5 |
| Example 9 | Polymerization Example 3 | 30 | TCD-3 (Example 1) | 44.2/55.8 | 30 | 1.0 |
| Example 10 | Polymerization Example 4 | 20 | TCD-3 (Example 2) | 55.6/44.4 | 52 | 0.75 |
| Example 11 | Polymerization Example 5 | 30 | TCD-3 (Example 2) | 55.6/44/4 | 52 | 1.0 |
| Example 12 | Polymerization Example 6 | 30 | TCD-3 (Example 2) | 55.6/44.4 | 25 | 2.0 |
| Example 13 | Polymerization Example 7 | 15 | TCD-3 (Example 3) | 33.0/67.0 | 60 | 0.5 |
| Example 14 | Polymerization Example 8 | 30 | TCD-3 (Example 3) | 33.0/67.0 | 60 | 0.5 |
| Comparative Example 1 | Comparative Polymerization Example 1 | 35 | TCD-3 (Comparative Example 1) | 94.9/5.1 | 45 | 0.5 |
| Comparative Example 2 | Comparative Polymerization Example 2 | 35 | TCD-3 (Comparative Example 1) | 94.9/5.1 | 60 | 0.5 |

| Example No. | Polymerization Example No. | Polymer yield (g/l) | Polymer composition (mol %) C2= | Polymer composition (mol %) TCDs | (Endo form/exo form ratio of TCD) | Intrinsic viscosity (dl/g)$^{(\eta)}$ | TMA softening temp. (°C.) | Flexural modulus (kg/cm$^2$) |
|---|---|---|---|---|---|---|---|---|
| Example 7 | Polymerization Example 1 | 35 | 60.7 | 39.3 | (41/59) | 0.37 | 180 | 34600 |
| Example 8 | Polymerization Example 2 | 54 | 70.3 | 29.7 | (43/57) | 0.57 | 135 | 30100 |
| Example 9 | Polymerization Example 3 | 43 | 77.4 | 22.6 | (43/57) | 0.49 | 93 | 26400 |
| Example 10 | Polymerization Example 4 | 45 | 64.5 | 35.5 | (56/44) | 0.38 | 172 | 32600 |
| Example 11 | Polymerization | 55 | 70.2 | 29.8 | (56/44) | 0.40 | 140 | 30600 |

TABLE 6-continued

| | | | | | | | | |
|---|---|---|---|---|---|---|---|---|
| | Example 5 | | | | | | | |
| Example 12 | Polymerization Example 6 | 42 | 80.7 | 19.3 | (58/42) | 0.30 | 81 | 25600 |
| Example 13 | Polymerization Example 7 | 44 | 63.4 | 36.6 | (32/68) | 0.38 | 161 | 35000 |
| Example 14 | Polymerization Example 8 | 57 | 72.0 | 28.0 | (32/68) | 0.56 | 120 | 31000 |
| Comparative Example 1 | Comparative Polymerization Example 1 | 45 | 70.0 | 30.0 | (93/7) | 0.60 | 111 | 27100 |
| Comparative Example 2 | Comparative Polymerization Example 2 | 41 | 63.0 | 37.0 | (95/5) | 0.49 | 147 | 31500 |

EXAMPLES 15-17

Polymerization Examples 9-11 and Comparative Example 3 (Comparative Polymerization Example 3)

Copolymerization of ethylene with 8-ethyl-tetracyclododecene-3 was carried out in the same way as in Example 7 by using materials (8-ethyl-tetracyclododecene-3) shown in Table 7.

Table 7 shows the results.

Table 7 shows that the copolymers obtained in Examples 15-17, using 8-ethyl-tetracyclododecene-3 having a large content of an exo form, are improved both in TMA softening temperature and flexural modulus as compared with the copolymer obtained in Comparative Example 3.

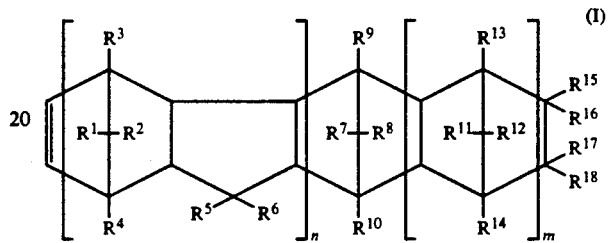

wherein $R^1$ to $R^{14}$ are independently a hydrogen atom, a halogen atom or a hydrocarbon group, $R^{15}$ to $R^{18}$ are independently a hydrogen atom, a halogen atom or a hydrocarbon group, or $R^{15}$ or $R^{16}$ and $R^{17}$ or $R^{18}$ may be bonded to each other to form a monocyclic or polycyclic group, or $R^{15}$ and $R^{16}$ or $R^{17}$ and $R^{18}$ may together form an alkylidene group only when n is 1, n is 0 or 1, and m is 0 or a positive integer, provided that m and n cannot be simultaneously zero,

TABLE 7

| Example No. | Polymerization Example No. | Amount of ethylene fed (l/hr) | TCDs Kind | TCDs Endo form/exo form ratio (mol %) | TCDs Amount (g/l) | $H_2$ Amount (l/hr) |
|---|---|---|---|---|---|---|
| Example 15 | Polymerization Example 9 | 35 | 8E-TCD-3 (Example 4) | 50.1/49.9 | 53 | 0.5 |
| Example 16 | Polymerization Example 10 | 35 | 8E-TCD-3 (Example 5) | 39.7/60.3 | 53 | 0.5 |
| Example 17 | Polymerization Example 11 | 35 | 8E-TCD-3 (Example 6) | 7.2/92.8 | 53 | 0.5 |
| Comparative Example 3 | Comparative Polymerization Example 3 | 35 | 8E-TCD-3 (Referential Example 2) | 97.3/2.7 | 53 | 0.5 |

| Example No. | Polymerization Example No. | Polymer yield (g/l) | Polymer composition (mol %) $C_2^=$ | Polymer composition (mol %) TCDs | Polymer composition (mol %) (Endo form/exo form ratio of TCD) | Polymer properties Intrinsic viscosity (dl/g)$^{(\eta)}$ | Polymer properties TMA softening temp. (°C.) | Polymer properties Flexural modulus (kg/cm$^2$) |
|---|---|---|---|---|---|---|---|---|
| Example 15 | Polymerization Example 9 | 43 | 70.7 | 29.3 | (51/49) | 0.58 | 129 | 31200 |
| Example 16 | Polymerization Example 10 | 45 | 71.0 | 29.0 | (38/62) | 0.63 | 128 | 31500 |
| Example 17 | Polymerization Example 11 | 40 | 68.5 | 31.5 | (8/92) | 0.55 | 120 | 30700 |
| Comparative Example 3 | Comparative Polymerization Example 3 | 47 | 70.1 | 29.9 | (97/3) | 0.65 | 108 | 26900 |

What is claimed is:

1. A cycloolefinic random copolymer:
(1) which is a copolymer formed from ethylene and an isomer mixture of up to 80 mol % of a cycloolefin having an endo form with at least 20 mol % of the cycloolefin having an exo form, the cycloolefin having the following formula (I)

(2) which has, based on a total of polymer units derived from the cycloolefin and polymer units derived from the ethylene, 10 to 90 mol % of the polymer units derived from the cycloolefin and 90 to 10 mol % of the polymer units derived from the ethylene, (3) wherein the polymer units derived from the cycloolefin have the following formula (II)

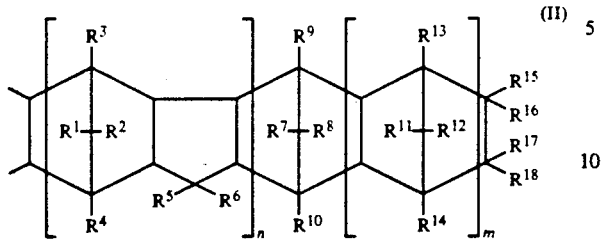

wherein $R^1$ to $R^{18}$, n and m are as defined as above, and (4) which has an intrinsic viscosity ($\eta$), measured in decahydronaphthalene at 135° C., of 0.05 to 10 dl/g.

2. A random copolymer according to claim 1, wherein the cycloolefin has the following formula (I-A)

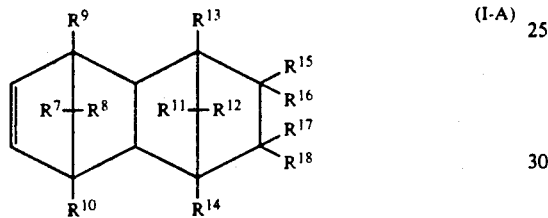

wherein $R^7$ to $R^{18}$ are as defined above, and the polymer unit thereof has the following formula (II-A)

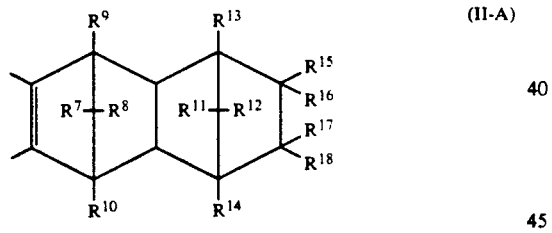

wherein $R^7$ to $R^{18}$ are as defined above.

3. A process for the production of a cycloolefin random copolymer according to claim 1 which comprises copolymerizing an isomer mixture of endo form and exo form cycloolefins of the formula (I) which comprises, based on the cycloolefin having an endo form and the cycloolefin having an exo form in total, up to 80 mol % of the cycloolefin having an endo form and at least 20 mol % of the cycloolefin having an exo form and ethylene in a hydrocarbon solvent or without any hydrocarbon solvent in the presence of a catalyst which is composed of a vanadium compound and an organoaluminum compound and is soluble in the hydrocarbon solvent or a cycloolefin of the isomer mixture.

4. A random copolymer:

(1) which is formed from ethylene and an isomer mixture of up to 80 mol % of a cycloolefin having an endo form with at least 20 mol % of the cycloolefin having an exo form, the cycloolefin having the following formula (I-B)

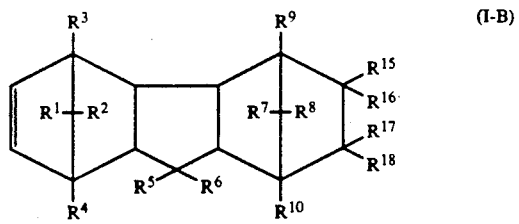

wherein $R^1$ to $R^{10}$ are independently a hydrogen atom, a halogen atom or a hydrocarbon group, $R^{15}$ to $R^{18}$ are independently a hydrogen atom, a halogen atom or a hydrocarbon group, or $R^{15}$ or $R^{16}$ and $R^{17}$ or $R^{18}$ may be bonded to each other to form a monocyclic or polycyclic group, or $R^{15}$ and $R^{16}$ or $R^{17}$ and $R^{18}$ may together form an alkylidene group, (2) which has, based on a total of polymer units derived from the cycloolefin and polymer units derived from the ethylene, 10 to 90 mol % of the polymer units derived from the cycloolefin and 90 to 10 mol % of the polymer units derived from the ethylene, (3) wherein the polymer units derived from the cycloolefin have the following formula (II-B)

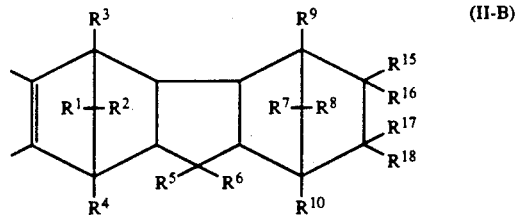

wherein $R^1$ to $R^{10}$ and $R^{15}$ to $R^{18}$ are as defined above, and (4) which has an intrinsic viscosity ($\eta$), measured in decahydronaphthalene at 135° C., of 0.05 to 10 dl/g 5. The random cycloolefinic copolymer of claim 1 wherein the isomer mixture comprises, based on the total of endo form and exo form cycloolefins, 70 to 5 mol % endo form cycloolefin and 30–95 mol % of exo form cycloolefin.

6. The random cycloolefinic copolymer of claim 1 wherein from 85 to 50 mol % of the polymer units are derived from ethylene, based on the total of polymer units.

7. The random cycloolefinic copolymer of claim 1 wherein n is 1.

8. The random cycloolefinic copolymer of claim 1 wherein n is 0.

* * * * *